US012310928B2

(12) United States Patent
Tashjian et al.

(10) Patent No.: US 12,310,928 B2
(45) Date of Patent: May 27, 2025

(54) ENTHESIS HEALING

(71) Applicant: UNIVERSITY OF UTAH RESEARCH FOUNDATION, Salt Lake City, UT (US)

(72) Inventors: Robert Z. Tashjian, Salt Lake City, UT (US); Peter N. Chalmers, Salt Lake City, UT (US); T. Wade Fallin, Hyde Park, UT (US); James M. Hotaling, Salt Lake City, UT (US)

(73) Assignee: UNIVERSITY OF UTAH RESEARCH FOUNDATION, Salt Lake City, UT (US)

( * ) Notice: Subject to any disclaimer, the term of this patent is extended or adjusted under 35 U.S.C. 154(b) by 388 days.

(21) Appl. No.: 17/099,224

(22) Filed: Nov. 16, 2020

(65) Prior Publication Data

US 2022/0151950 A1     May 19, 2022

(51) Int. Cl.
| | | |
|---|---|---|
| A61K 31/05 | (2006.01) | |
| A61B 17/00 | (2006.01) | |
| A61B 17/04 | (2006.01) | |
| A61B 17/06 | (2006.01) | |
| A61K 9/70 | (2006.01) | |
| A61K 45/06 | (2006.01) | |
| A61L 17/00 | (2006.01) | |
| A61P 19/00 | (2006.01) | |
| A61P 21/00 | (2006.01) | |

(52) U.S. Cl.
CPC ............ *A61K 31/05* (2013.01); *A61K 9/7023* (2013.01); *A61K 45/06* (2013.01); *A61L 17/005* (2013.01); *A61P 19/00* (2018.01); *A61P 21/00* (2018.01); *A61B 2017/00893* (2013.01); *A61B 17/0401* (2013.01); *A61B 17/06166* (2013.01)

(58) Field of Classification Search
CPC .... A61K 31/568; A61L 2430/10; A61P 19/04
See application file for complete search history.

(56) References Cited

U.S. PATENT DOCUMENTS

| | | | |
|---|---|---|---|
| 4,450,150 A | 5/1984 | Sidman | |
| 5,460,820 A | 10/1995 | Ebert et al. | |
| 5,783,208 A | 7/1998 | Venkateshwaran et al. | |
| 5,836,935 A | 11/1998 | Ashton et al. | |
| 6,139,873 A | 10/2000 | Hughes et al. | |
| 6,187,742 B1 | 2/2001 | Wozney et al. | |
| 6,228,852 B1 | 5/2001 | Shaak | |
| 6,689,153 B1 | 2/2004 | Skiba | |
| 6,936,270 B2 | 8/2005 | Watson et al. | |
| 7,625,920 B2 | 12/2009 | Meissner et al. | |
| 7,741,273 B2 | 6/2010 | McKay | |
| 7,763,582 B2 | 7/2010 | Lin et al. | |
| 7,776,826 B2 | 8/2010 | Vignery et al. | |
| 7,976,858 B2 | 7/2011 | Hotchkiss et al. | |
| 8,202,531 B2 | 6/2012 | McKay | |
| 8,354,375 B2 | 1/2013 | Vukicevic et al. | |
| 8,501,690 B2 | 8/2013 | Stark | |
| 8,557,271 B2 | 10/2013 | Kimble et al. | |
| 8,728,509 B2 | 5/2014 | McKay | |
| 8,870,954 B2 | 10/2014 | Lynch et al. | |
| 8,895,540 B2 | 11/2014 | Dimauro et al. | |
| 8,933,028 B2 | 1/2015 | Stark | |
| 9,440,009 B2 | 9/2016 | Armbruster et al. | |
| 9,445,901 B2 | 9/2016 | Tunc et al. | |
| 9,616,205 B2 | 4/2017 | Nebosky et al. | |
| 9,623,152 B2 | 4/2017 | Ogilvie et al. | |
| 9,623,222 B2 | 4/2017 | McKay | |
| 9,642,658 B2 | 5/2017 | Boyd et al. | |
| 9,642,891 B2 | 5/2017 | Hart et al. | |
| 10,022,233 B1 | 7/2018 | Gall et al. | |
| 10,188,441 B2 | 1/2019 | Kim et al. | |
| 10,258,566 B2 | 4/2019 | Hart et al. | |
| 10,349,993 B2 | 7/2019 | Nebosky et al. | |
| 10,369,098 B2 | 8/2019 | Kassab et al. | |
| 10,441,567 B2 | 10/2019 | Zhi | |
| 10,456,450 B2 | 10/2019 | Hart et al. | |
| 10,610,570 B2 | 4/2020 | Riester et al. | |
| 10,624,996 B2 | 4/2020 | Gall et al. | |
| RE49,219 E | 9/2022 | DiMauro et al. | |
| 11,660,373 B2 | 5/2023 | Carter et al. | |

(Continued)

FOREIGN PATENT DOCUMENTS

| | | | |
|---|---|---|---|
| WO | 2013/119582 A1 | 8/2013 | |
| WO | WO 2018/031454 | * 2/2018 | |

OTHER PUBLICATIONS

Alberts D.S. et al., "Randomized phase 3 trial of interferon gamma-1b plus standard carboplatin/paclitaxel versus carboplatin/paclitaxel alone for first-line treatment of advanced ovarian and primary peritoneal carcinomas: results from a prospectively designed analysis of progression-free survival", Gynecologic Oncology, vol. 109, No. 2, Mar. 2008, pp. 174-181.

Cornetta K. et al., "A retroviral vector expressing human interferon gamma upregulates MHC antigen expression in human breast cancer and leukemia cell lines", Cancer Gene Therapy, vol. 1, No. 1, 1994, pp. 91-98.

Martini M. et al., "IFN-?-mediated upmodulation of MHC class I expression activates tumor-specific immune response in a mouse model of prostate cancer", Vaccine, vol. 28, No. 20, Mar. 19, 2010, pp. 3548-3557.

(Continued)

*Primary Examiner* — Sahar Javanmard
(74) *Attorney, Agent, or Firm* — Workman Nydegger

(57) ABSTRACT

Disclosed are devices and methods for improving healing of an enthesis. An effective amount of a composition comprising one or more sex steroids and/or sex steroid equivalents is locally administered at the site of a repaired enthesis. The composition causes upregulation of one or more chondrogenic, angiogenic, and/or tendon modulation genes, resulting in improved healing of the enthesis. The improved enthesis healing occurs even where the subject has normal levels of sex hormones.

20 Claims, 7 Drawing Sheets

(56) References Cited

U.S. PATENT DOCUMENTS

| | | |
|---|---|---|
| 11,680,094 B2 | 6/2023 | Cao |
| 2004/0034357 A1 | 2/2004 | Beane et al. |
| 2006/0093646 A1 | 5/2006 | Cima et al. |
| 2007/0275035 A1 | 11/2007 | Herman et al. |
| 2008/0228193 A1 | 9/2008 | Matityahu |
| 2008/0234727 A1 | 9/2008 | Garigapati et al. |
| 2009/0177229 A1 | 7/2009 | Gulotta et al. |
| 2011/0238016 A1 | 9/2011 | Hotchkiss et al. |
| 2013/0144250 A1 | 6/2013 | Schwarz et al. |
| 2014/0056960 A1 | 2/2014 | Nanchahal et al. |
| 2014/0315847 A1 | 10/2014 | Peck et al. |
| 2017/0165077 A1 | 6/2017 | McDonnell |
| 2017/0224970 A1 | 8/2017 | Munster et al. |
| 2019/0083231 A1 | 3/2019 | Gazit et al. |
| 2019/0185556 A1 | 6/2019 | Ominsky et al. |
| 2020/0170640 A1 | 6/2020 | Wilson-Wirth et al. |
| 2022/0226544 A1 | 7/2022 | Hotchkiss et al. |

OTHER PUBLICATIONS

Street D. et al., "Interferon-? Enhances Susceptibility of Cervical Cancer Cells to Lysis by Tumor-Specific Cytotoxic T Cells", Gynecologic Oncology, vol. 65, No. 2, 1997, pp. 265-272.

Barrett-Connor et al., "A Two-Year, Double-Blind Comparison of Estrogen-Androgen and Conjugated Estrogens in Surgically Menopausal Women", Journal of Reproductive Medicine, vol. 44, No. 2, Dec. 1999, pp. 1012-1020.

Guthrie et al., "The relative effect of endogenous estradiol and androgens on menopausal bone loss: a longitudinal study", Osteoporos Int, Mar. 24, 2004, vol. 15, pp. 881-886.

Hofbauer et al., "Androgen effects on bone metabolism: recent progress and controversies", European Journal of Endocrinology, 1999, vol. 140, pp. 271-286.

Non-Final Office Action received for U.S. Appl. No. 18/732,532, mailed on Aug. 15, 2024, 11 pages.

Savvas et al., "Increase in bone mass after one year of percutaneous oestradiol and testosterone implants in post-menopausal women who have previously received received long-term oral oestrogens", British Journal of Obstetrics and Gynaecology, Sep. 1992, vol. 99, pp. 757-760.

Savvas et al., "Skeletal Effects of Oral Oestrogen Compared with Subcutaneous Oestrogen and Testosterone In Postmenopausal Women", BMJ: British Medical Journal, vol. 297, No. 6644, Jul. 30, 1988, pp. 331-333.

Watts et al., "Comparison of Oral Estrogens and Estrogens Plus Androgen on Bone Mineral Density, Menopausal Symptoms, and Lipid-Lipoprotein Profiles in Surgical Menopause", Obstetrics & Gynecology, vol. 85, No. 4, Apr. 1995, pp. 529-537.

\* cited by examiner

ENTHESIS HEALING

CROSS-REFERENCE TO RELATED APPLICATIONS

N/A.

BACKGROUND

Technical Field

This disclosure generally relates to enthesis repair, specifically, the restoration of an injured or degenerated enthesis to a state that more closely resembles the normal physiological state of a native, healthy enthesis. The disclosure further relates to methods of using sex steroids and their equivalents to improve the quality of healing of a damaged or injured enthesis.

Related Technology

An enthesis is the attachment site for tendons, ligaments or joint capsules into bones. Tendons take origin from a bone on one side of a joint. Extending toward another bone on the opposite side of the joint, the tendon transitions into muscle and then back into tendon tissue to attach to the bone on the opposite side of the joint. The purpose of a muscles is to contract and shorten, therefore pulling the bone on the opposite side of a joint through the tendons to move the bones and subsequently move the joint. Ligaments and joint capsules take origin from one side of a joint and then insert into a bone on the other side of the same joint. Ligaments and joint capsules serve to stabilize a joint and to control how the joint moves.

The enthesis is a tissue gradient, transitioning sequentially, starting at the tendon side, from: 1) parallel collagen fibers with oriented fibroblasts, 2) fibrocartilaginous tissue with chondrocytes, 3) calcified fibrocartilage, and 4) bone. Entheses that are commonly injured and surgically repaired include Achilles tendon, rotator cuff tendon, distal biceps and triceps tendon, pectoralis major tendon, flexor and extensor tendon, wrist extensor and flexor tendon, hip abductor tendon, proximal hamstring tendon, patella tendon, quadriceps tendon, peroneal tendon, toe flexor and extensor tendon, anterior cruciate ligament, posterior cruciate ligament, knee medial and lateral collateral ligaments, anterior talofibular ligament, the calcaneofibular ligament, and the posterior talofibular ligament, anterior inferior tibiofibular ligament, posterior inferior tibiofibular ligament, ankle deltoid and spring ligament, acromioclavicular ligament, coracoclavicular ligaments, sternoclavicular ligaments, elbow lateral collateral ligaments, elbow medial collateral ligament, radial annular ligament, ligaments of the wrist, plantar plate, and collateral ligaments of the fingers, thumbs and toes.

As an example of surgical repair of an injured enthesis, during a typical repair of a tendon enthesis, suture material is passed through the tendon and then anchored to the bone using either suture anchors or bone tunnels. For example, during a rotator cuff repair (RCR), high strength suture material is passed into the substance of the tendon via open surgery or arthroscopically in simple or mattress fashion. The suture may be attached to a suture anchor which has been placed in the bone prior to passage of the suture. Once the suture is passed, it is tied in a knot to secure the tendon tissue to the bone. Alternatively, free suture is passed into the tendon and then passed into a suture anchor which is then inserted into the bone, with subsequent tensioning of the suture fixing the tendon to the bone.

Regardless of the specific anatomic enthesis, a certain percentage of surgically repaired entheses suffer a re-tear due to incomplete or poor healing of the enthesis. For example, despite significant improvements in the biomechanical strength of rotator cuff repair constructs over the last three decades, healing rates after rotator cuff repair have not significantly improved during that time. The first reported healing rates after rotator cuff repair were published in 1991, which reported 80% healing rates of single tendon tears and 50% healing rates of two tendon tears. (D T Harryman, A Mack, K Y Wang, S E Jackins, M L Richardson, F A Matsen. Repairs of the rotator cuff. Correlation of functional results with integrity of the cuff. J Bone Joint Surg 1991). Since that time, hundreds of authors have reported on healing rates after rotator cuff repair. Even with improved surgical techniques such as bridging double row repair constructs, healing rates have been reported to be identical. For example, a publication in 2011 reported 78% healing for single tendon tears and 50% healing for multiple tendon tears. (Cho N S, Lee B G, Rhee Y G. Arthroscopic rotator cuff repair using a suture bridge technique: is the repair integrity actually maintained? Am J Sports Med. 2011 October).

The primary failure of repair healing is the inability for a tendon to heal and reconstitute the normal physiological enthesis. As discussed above, the normal enthesis transitions from tendon/ligament, to uncalcified cartilage, to calcified cartilage, to bone. In the setting of a surgical tendon repair, the transition zone from tendon to bone after healing is disorganized scar tissue which includes collagen fibers in a disorganized pattern and large areas of uncalcified cartilage. Attempts have been made to reconstitute the normal enthesis utilizing biologics. Vascular endothelial growth factor A (VEGFA), fibroblast growth factor 2 (FGF-2), platelet derived growth factor-BB (PDGF-BB) and transforming growth factor beta1 (TGF-beta1) have all been shown to positively influence histologic or biomechanical characteristics after rotator cuff repair in mouse and rat models. However, reconstitution of the normal enthesis has not been possible. (see, e.g., Arimura H, Shukunami C, Tokunaga T, Karasugi T. Okamoto N, Taniwaki T, Sakamoto H, Mizuta H, Hiraki Y. TGF-beta1 improves biomechanical strength by extracellular matrix accumulation without increasing the number of tenogenic lineage cells in a rat rotator cuff repair model. Am J Sports Med 2017).

The influence of hormones, specifically estrogen, have been evaluated in hormone deficiency animal models for tendon development and healing. Animal models have supported the conclusion that estrogen deficiency results in inferior tendon metabolism as well as inferior tendon healing. (Torricelli P, Veronesi F, Pagani S, Maffulli N, Masiero S, Frizzier A, Fini M. In vitro tenocyte metabolism in aging and estrogen deficiency. Age. 2013). Recent evidence supports the conclusion that selective estrogen receptor modulator supplementation in an estrogen deficient animal can improve the biomechanical strength and overall quality of rotator cuff repairs histologically with significantly improved histomorphometric scores. (Kim D M, Shim I K, Shin M J, Choi J H, Lee Y N, Jeon I H, Kim H, Park D, Kholinne E, Koh K H. A Combination Treatment of Raloxifene and Vitamin D Enhances Bone-to-Tendon Healing of the Rotator Cuff in a Rat Model. Am J Sports Med. 2020 July).

However, despite these advances, several problems remain in the field of enthesis repair. In particular, re-tear injuries due to incomplete or poor healing of the enthesis are common even in subjects that do not necessarily have an estrogen deficiency. Thus, while correcting known deficiencies may help a small subset of patients, it does not represent a treatment generally applicable to other patients suffering from an enthesis injury. Accordingly, there is an ongoing need to provide new devices and methods of treatment for enthesis injuries and/or degeneration, and to improve the healing response associated with associated surgical repairs.

SUMMARY

Disclosed herein are devices and methods for improving healing of an enthesis. An effective amount of a composition comprising one or more sex steroids (e.g., estrogen, androgen) and/or sex steroid equivalents (e.g., selective estrogen receptor modulator, selective androgen receptor modulator) is administered at an enthesis site. The composition provides an increase in at least one sex steroid in the subject which leads to improved healing of the enthesis. Beneficially, improved enthesis healing occurs even in subjects with normal levels of sex hormones.

While correcting deficiencies of sex steroids can bring levels closer to normal and result in improved outcomes, the rate of healing failure and re-tear injuries remains high even among subjects without sex steroid deficiencies and among subjects with deficiencies corrected through supplementation. This disclosure teaches that the administration of one or more sex steroids and/or sex steroid equivalents to a subject with otherwise normal levels of sex steroids unexpectedly promotes improved enthesis healing. This is surprising given the fact that any positive effects of sex steroid supplementation on enthesis healing would be expected to significantly diminish once levels are brought to normal levels (or where levels were already at normal levels).

In preferred embodiments, the composition is administered locally at the target enthesis site rather than systemically. Although systemic administration has been the conventional approach for raising levels of sex steroids in subjects that are deficient in one or more sex steroids, such systemic administration is likely to be associated with one or more undesirable side effects. For subjects that are not deficient in sex steroids, the importance of local administration becomes even more significant.

The administered composition can cause upregulation of one or more chondrogenic, angiogenic, and/or tendon modulation genes, resulting in improved healing of the enthesis.

In some embodiments, the composition is administered by way of a drug-eluting implant implanted at or near the site of the enthesis, a drug-loaded textile positioned at or near the site of the enthesis, a drug-loaded patch positioned at or near the site of the enthesis, injection of an extended release formula comprising the composition, or combination thereof. The composition can thereby elute during at least a portion of a healing period of the enthesis to sustain improved enthesis healing.

This summary is provided to introduce a selection of concepts in a simplified form that are further described below in the detailed description. This summary is not intended to identify key features or essential features of the claimed subject matter, nor is it intended to be used as an indication of the scope of the claimed subject matter.

BRIEF DESCRIPTION OF THE DRAWINGS

Various objects, features, characteristics, and advantages of the invention will become apparent and more readily appreciated from the following description of the embodiments, taken in conjunction with the accompanying drawings and the appended claims, all of which form a part of this specification. In the drawings:

DETAILED DESCRIPTION

Introduction

Figure 1:
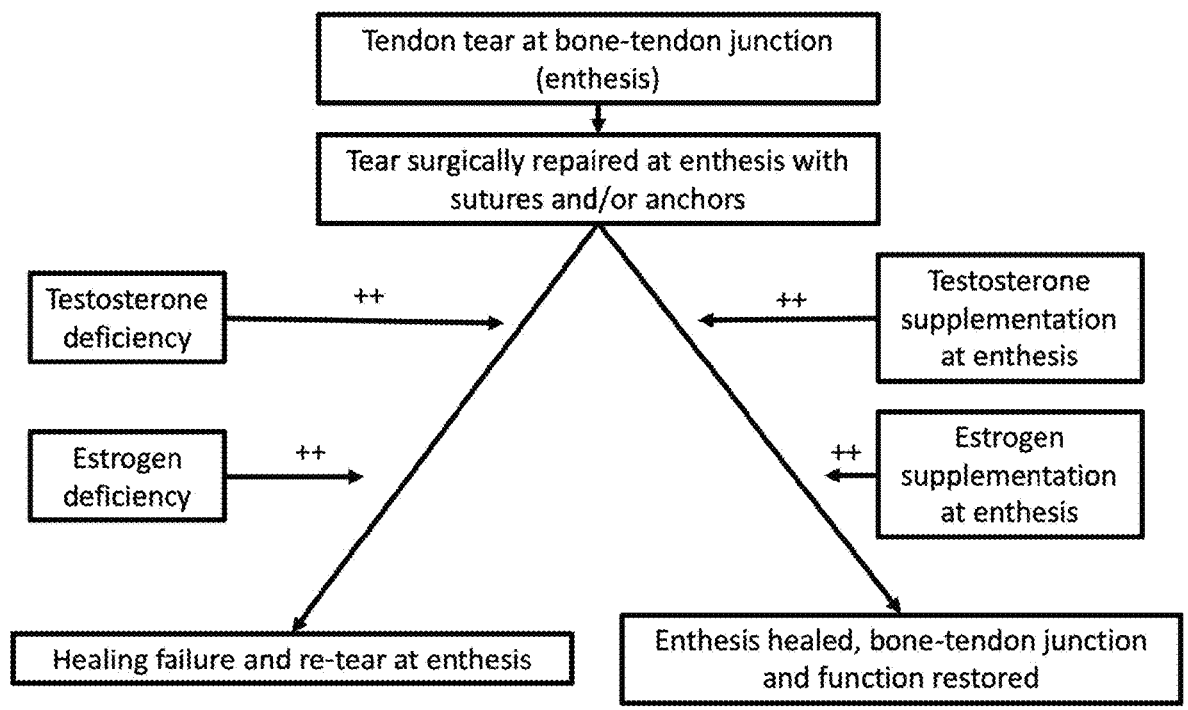
FIG. 1 is a schematic drawing of a simplified scheme of enthesis healing with sex steroid deficiency and supplementation.

The present disclosure is directed to devices and methods for improving enthesis healing through administration of one or more sex steroids and/or sex steroid equivalents to a target enthesis site. In particular, the present disclosure is directed to devices and methods for improving the healing of an enthesis in a subject with otherwise normal levels of sex steroids through the local administration of one or more sex steroids and/or sex steroid equivalents at the target enthesis site. As described in more detail below, the inventors have discovered that local administration of one or more sex steroids and/or sex steroid equivalents to a target enthesis beneficially improves healing even in a subject that does not have a deficiency in the sex steroid(s) intended to be enhanced via the administered treatment.

As further described below, the one or more sex steroids and/or sex steroid equivalents are administered locally at the target enthesis site rather than systemically. Where subjects are deficient in a particular sex steroid, systemic administration has been the conventional method of administration. However, for subjects that are not deficient, systemic administration is likely to be associated with one or more undesirable side effects, potentially including higher risk of infection (see Example 4 below). Systemic administration has typically been the easiest and most straightforward means of administration for subjects known to have a deficiency, but with the beneficial discovery that sex steroids and/or sex steroid equivalents can improve healing in non-deficient subjects, the importance of local administration becomes even more significant.

Definitions

For purposes of interpreting this specification, the following definitions will apply. In the event that any definition set forth below conflicts with any document incorporated herein by reference, the definition set forth below shall control. The term "sex steroid" shall mean the endogenous sex steroid groups of estrogens and androgens. The term "sex steroid equivalent" includes synthetic or synthetically modified sex steroids, as well as compounds that function to promote levels of sex steroids within the body via receptor modulation (e.g., selective sex steroid receptor modulators), inhibiting breakdown or conversion of sex steroids, and the like. Occasionally, the term "drug" or "drug composition" is used as shorthand for "one or more sex steroids or sex steroid equivalents" or for a composition containing the one or more sex steroids or sex steroid equivalents (e.g., along with a carrier).

A subject with "normal" levels of a particular sex steroid, as opposed to a deficient level, is a subject with testable levels of the sex steroid that fall within a normal range as defined in medical literature and/or by a relevant medical organization or government agency. For example, the Food and Drug Administration (FDA) defines a serum testosterone level of 300 to 1,000 ng/dL as normal for an adult man. For women, normal levels are typically considered to range from 15 to 70 ng/dL. Normal levels of estradiol for a premenopausal adult woman are typically about 15 to 350 pg/ml. For men, normal levels of estradiol are typically about 10 to 40 pg/ml. Those skilled in the art can readily consult the literature to determine normal ranges for other sex steroids and/or for particular types of subjects.

An "effective dose" or "effective amount" is a dose that provides measurable therapeutic benefits when administered to a subject using one of the administration methods described herein. In particular, an effective dose of one or more sex steroids and/or sex steroid equivalents is a dose that provides a measurable improvement to the healing of an enthesis as compared to an enthesis not treated with the sex steroid and/or sex steroid equivalents. Specific, exemplary dosages are provided herein; however, an effective dose may lie outside the specifically described examples depending on particulars such as subject anatomy, repair procedure requirements, extent of enthesis damage, and the like.

Treatment Method Overview

FIG. 1 schematically illustrates a scheme of enthesis healing (or lack thereof) under circumstances of sex steroid deficiency and under circumstances of sex steroid supplementation. As shown, following enthesis repair with sutures and/or anchors, a sex steroid deficiency (e.g., testosterone and/or estrogen) is correlated with healing failure and re-tear at the enthesis. On the other hand, sex steroid supplementation (e.g., testosterone and/or estrogen) to correct the deficiency is a correlation with improved outcomes.

As discussed above, while correcting deficiencies of sex steroids can bring levels closer to normal and result in improved outcomes, the rate of healing failure and re-tear injuries remains high even among subjects without sex steroid deficiencies and among subjects with deficiencies corrected through supplementation. The inventors have now unexpectedly discovered that the administration of one or more sex steroids and/or sex steroid equivalents to a subject with otherwise normal levels of sex steroids promotes improved enthesis healing. This is surprising given the fact that any positive effects of sex steroid supplementation on enthesis healing would be expected to significantly diminish once levels are brought to normal levels (or where levels were already at normal levels). In other words, while correcting a deficiency may be expected to correct healing failures directly associated with the deficiency, going above normal levels would not be expected to provide further improvements in outcomes.

Figure 2:
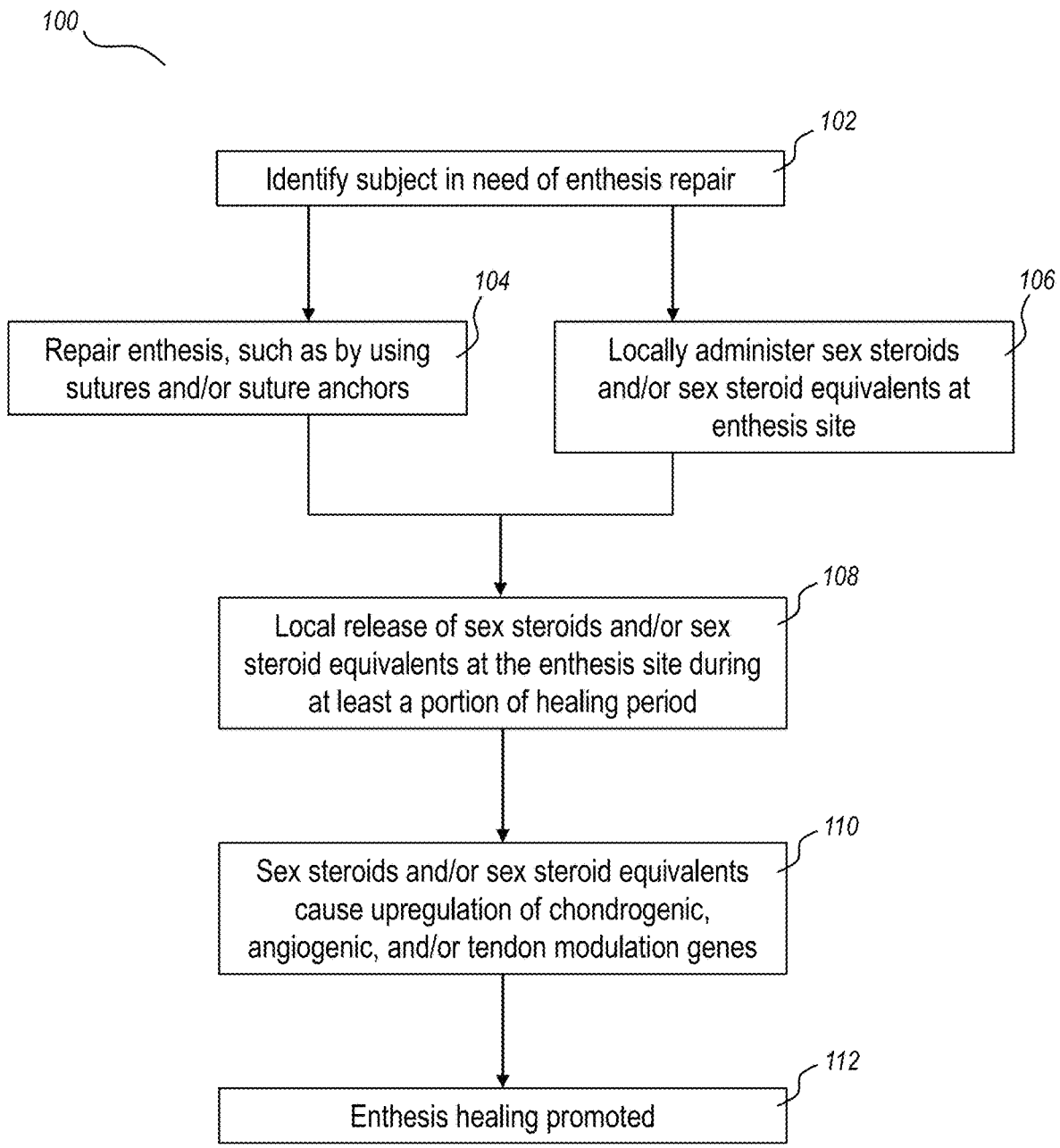
FIG. 2 illustrates a method for treating a subject to promote healing of an enthesis following repair of the enthesis.

FIG. 2 illustrates a method 100 of improving enthesis healing in a subject in need thereof. In the method, a first step 102 identifies a subject in need of enthesis repair. In most embodiments, the subject will not have a sex steroid deficiency, at least not in the one or more sex steroids intended to be enhanced via administration of the one or more sex steroids and/or sex steroid equivalents. Previously, such subjects were not believed to stand to benefit from administration of sex steroids and/or equivalents. The present invention has beneficially discovered that such subjects can indeed benefit from the treatment steps outlined herein.

Step 104 repairs the enthesis, such as through suture and/or suture anchor-based repair techniques, other enthesis repair techniques known in the art, or combination thereof. The repair site may be any enthesis subject to repair, including, but not limited to: Achilles tendon, rotator cuff tendon, distal biceps and triceps tendon, pectoralis major tendon, flexor and extensor tendon, wrist extensor and flexor tendon, hip abductor tendon, proximal hamstring tendon, patella tendon, quadriceps tendon, peroneal tendon, toe flexor and extensor tendon, anterior cruciate ligament, posterior cruciate ligament, knee medial and lateral collateral ligaments, anterior talofibular ligament, the calcaneofibular ligament, the posterior talofibular ligament, anterior inferior tibiofibular ligament, posterior inferior tibiofibular ligament, ankle deltoid and spring ligament, acromioclavicular ligament, coracoclavicular ligaments, sternoclavicular ligaments, elbow lateral collateral ligaments, elbow medial collateral ligament, radial annular ligament, ligaments of the wrist, plantar plate, and collateral ligaments of the fingers, thumbs and toes.

Step 106 locally administers sex steroids and/or sex steroid equivalents at the enthesis site. As described in more detail below, local administration may be accomplished via drug-eluting implant placed near the enthesis (e.g., sutures themselves, anchors themselves, other screws/plugs, textiles, fibers, patches, wraps), direct application of slow-release prodrug or drug depot composition, or combination thereof.

Steps 104 and 106 may be performed substantially simultaneously or may be performed sequentially so long as the sex steroids and/or sex steroid equivalents are administered close enough in time to the repair procedure to allow the positive effects to take place (e.g., within 1 to 30 days). For example, where an implant is utilized as a delivery vehicle for the sex steroids and/or sex steroid equivalents, placement of the implant typically happens during the repair procedure. Additionally, or alternatively, administration could take place sometime after the repair procedure. For example, injections at or near the enthesis repair site may occur following the repair procedure. In another example, an implant may be placed near the target enthesis during a separate procedure either before or after the repair procedure itself.

In step 108, sex steroids and/or sex steroid equivalents are locally released at the enthesis site during at least a portion of the healing period. The healing period may vary according to the particular subject, particular procedure, particular enthesis repaired, amount of enthesis damage repaired, and the like, but can typically range from about 12 to 16 weeks.

The local administration is preferably configured to provide release of sex steroids and/or sex steroid equivalents for a substantial portion of the healing period. For example, the sex steroids and/or sex steroid equivalents may elute at effective doses for a time period of at least about 30% of the healing period, or more preferably at least about 50% of the healing period, or even more preferably at least about 70% of the healing period.

The mechanism for delivering the sex steroids and/or sex steroid equivalents may be configured to provide substantially zero-order release kinetics. Some embodiments may utilize other release profiles. For example, some embodiments may provide an initial higher release bolus to "kick-start" effects followed by a slower release period.

In step 110, the sex steroids and/or sex steroid equivalents cause upregulation of one or more genes associated with enthesis healing, such as one or more chondrogenic, angiogenic, and/or tendon modulation genes. In step 112, healing of the enthesis is promoted as a result of the previous steps. Enthesis healing following the treatment method 100 outlined herein is expected to be greater than enthesis healing following conventional enthesis repair without supplementation of a sex steroid and/or sex steroid equivalent.

In other words, all else being equal, the treatment method 100 is expected to provide a repaired and healed enthesis that more closely resembles a natural (i.e., non-repaired and non-injured) enthesis as compared to an enthesis subjected to a conventional repair procedure. As a result, the number of re-tear injuries in subjects treated with method 100 is expected to be reduced as compared to the number of re-tear injuries following conventional treatment.

Sex Steroids & Equivalents

Sex steroids are vertebrate animal steroid hormones that interact with sex steroid hormone receptors. Sex steroids can be classified into two major categories: estrogens and androgens. Endogenous estrogens include estrone, estradiol, and estriol. Endogenous androgens include testosterone, dihydrotestosterone, and androstenedione. Exogenous estrogens include synthetic alternatives, derivatives, estrogen esters, and estrogen ethers. Exogenous androgens include synthetic alternatives, derivatives, androgen esters, and androgen ethers.

Sex steroid equivalents can include compounds that function to promote levels of sex steroids within the body via receptor modulation (e.g., selective sex steroid receptor modulators), inhibiting breakdown or conversion of sex steroids, and the like. Selective estrogen receptor modulators include afimoxifene, arzoxifene, bazedoxifene, clomifene, femarelle, lasofoxifene, ormeloxifene, tamoxifen, toremifene, analogs, and derivatives thereof. Selective androgen receptor modulators include enobosarm, and analogs or derivatives thereof. These chemicals interact with receptors that are expressed in nearly all tissues and create effects within nearly every human body system.

Any of the foregoing sex steroids (endogenous or exogenous), sex steroid equivalents, or combination thereof, may be utilized for local administration according to the present description. Although the particular selection of one or more sex steroids and/or sex steroid equivalents likely depends on the particular subject and/or enthesis being treated, it is expected that combination therapies combining both androgens and estrogens will promote healing to a greater degree than either alone.

It is further expected that androgens (and/or androgen equivalents) may be somewhat preferred over estrogens (and/or estrogen equivalents). Thus, where treatments do not combine both an androgen and an estrogen, one or more androgens and/or androgen equivalents may be preferred. Similarly, combination treatments may be primarily formulated to increase androgens and only secondarily formulated to increase estrogens.

In some embodiments, the one or more sex steroids and/or sex steroid equivalents may be combined with other drugs to increase the overall effectiveness, deliverability, or potency of the administered compositions. For example, the one or more sex steroids and/or sex steroid equivalents may be combined with an aromatase inhibitor (e.g., to prevent the conversion of testosterone to estrogen and thereby promote the effectiveness of administered testosterone).

Dosing

Table 1 shows available forms of estrogens or estrogen equivalents, dosing schedule for systemic administration, half-life, volume per dose, and concentration. While estrogen is typically dosed at 1 to 40 mg systemically, depending upon the ester used, dosing of about 0.05 mg to about 8 mg, or more preferably about 0.1 mg to about 4 mg is used in the present embodiments for local administration of one or more estrogen or estrogen equivalents. Concentrations may be similar to those used in systemic administration.

TABLE 1

Available forms of estrogen;

| Name | Dosing Schedule (systemic) | Half-life | Volume/ Dose | Concentration |
| --- | --- | --- | --- | --- |
| Raloxifene (SERM) | Daily | 28 hours | 60 ml | NA (pill) |
| Tamoxifen (SERM) | Daily | 5-7 days | 20-40 ml | NA (pill) |
| Clomiphene (SERM) | Every other day | 5 days | 50 ml | NA (pill) |
| Estradiol cypionate | 3-4 weeks | 8-10 days | 1-5 ml | Up to 5 mg/ml |
| Estradiol benzoate | 2-4 days | 2-5 days | 0.5-1.5 ml | Up to 25 mg/ml |
| Estradiol dipropionate | Weekly, biweekly | >5 days | 2-20 ml | Up to 5 mg/ml |
| Estradiol enanthate | Monthly | 5-8 days | 5-50 ml | Up to 10 mg/ml |
| Estradiol undecylate | 3-4 weeks | 1-2 mon | 50-100 ml | Up to 100 mg/ml |
| Estradiol valerate | Monthly | 4-5 days | 10-20 ml | Up to 40 mg/ml |

NA = not applicable as the medication is typically given in pill form instead of as an injectable.

Table 2 shows available forms of testosterone or testosterone equivalents, dosing schedule for systemic administration, half-life, volume per dose, and concentration. While testosterone is typically dosed at 100 to 800 mg systemically, depending upon the ester used, dosing of about 2.5 mg to about 200 mg, or more preferably about 5 mg to about 100 mg is used in the present invention for local administration of one or more testosterone or testosterone equivalents. Concentrations may be similar to those used in systemic administration.

TABLE 2

Available forms of testosterone

| Name | Dosing Schedule (systemic) | Half-life | Volume/Dose | Concentration |
|---|---|---|---|---|
| Testosterone enanthate | 1-2 weeks | 4.5 days | 50-200 ml | 200 mg/ml |
| Testosterone cypionate | 2-4 weeks | 8 days | 50-400 ml | 200 mg/ml |
| Testosterone propionate | 3-7 days | 2 days | 25-75 ml | 200 mg/ml |
| Testosterone undecanoate (PO) | Twice daily | 100 min | 237-792 ml | ml mg/tablet |
| Testosterone undecanoate (IM) | 10 weeks | 34 days | 750 ml | 250 mg/ml |
| Ligandrol | Daily | 24-36 hrs | 5-20 ml | 20 mg/ml |
| Enobosarm | 3 times daily | 100 min | 11-33 ml | 11 mg/2 sprays |

The lower doses utilized in the devices and methods disclosed herein beneficially reduce the risk of unwanted side effects associated with sex steroid supplementation. Despite the significantly reduced doses as compared to conventional systemic administration, the local administration techniques described herein promote healing at the target enthesis. Further, at the low overall doses, even if some amount of the administered sex steroid and/or equivalents gets into systemic circulation in the subject, it is unlikely to cause significant systemic effects.

In one exemplary embodiment, while estradiol cypionate is typically systemically dosed at 10 mg in a volume of 2 ml, local administration instead utilizes 1 mg in a volume of 0.2 ml. The lower dose may be eluted locally to improve enthesis healing while avoiding negative effects associated with systemic administration and/or larger doses.

In another exemplary embodiment, while testosterone undecanoate is typically systemically dosed at 750 mg in a volume of 3 ml, local administration instead utilizes 75 mg in a volume of 0.3 ml. The lower dose may be eluted locally to improve enthesis healing while avoiding negative effects associated with systemic administration and/or larger doses.

Local Administration

Surgical Repair

Typical surgical repair of an enthesis includes placement of either bone tunnels or suture anchors into the bone in which the tendon is to be repaired. Suture material is then passed through the tendon substance and then the sutures are passed through the bone tunnels and tied. If anchors are used, the anchors may be preloaded with suture. The suture is passed through the tendon after the anchors are placed and then tied. For anchors that are not preloaded, suture is passed through the tendon then the anchor is loaded with the sutures and placed into the bone. The suture is then tied or tensioned and the suture is locked into place.

In some embodiments, the one or more sex steroids and/or sex steroid equivalents are placed into the surgical site as part of the foregoing repair construct to improve tendon healing. This may be accomplished, for example, using a drug eluting implant placed in proximity to the enthesis, drug-loaded textile, drug-loaded patch, prodrug or drug depot, or combination thereof.

Drug-Eluting Implant

In some embodiments, the repair suture itself is loaded with the one or more sex steroids and/or sex steroid equivalents and elutes at the target site. Additionally, or alternatively, one or more suture anchors used as part of the repair construct are loaded with the one or more sex steroids and/or sex steroid equivalents. An example of a suture anchor capable of eluting drugs is provided in U.S. patent publication No. 2009/0177229A1, which is incorporated in its entirety by this reference.

In some embodiments, a separate drug eluting implant is placed in proximity to the enthesis, either in addition to or as an alternative to eluting sutures and/or anchors. The implant may be placed, for example, in a formed cavity in a bone or attached to or placed adjacent to soft tissue near the target enthesis. The drug eluting implant may be comprised of exterior surfaces bounding a cavity where the drug is stored. The exterior surfaces, or at least a portion thereof, includes a port, a series of ports, or overall porosity that controls the elution rate of the drug.

The drug eluting implant may be comprised of titanium alloy, magnesium alloy, or any other suitable biocompatible metal. Additionally, or alternatively, the drug eluting implant may be comprised of: polyetheretherketone, polyetherketoneketone, collagen, bone, polyethylene, polyester, polypropylene, silk, nylon, polyglyconate, polydioxanone, polyglactin, polyglycolic acid, polylactic acid, polydioxanone, polydroxyalkanoate, poliglecaprone, polycaprolactone, carbon fiber, hydroxyapatite, tricalcium phosphate, bioglass, other biocompatible materials, or combinations thereof.

In one embodiment, the drug-eluting implant is sized for implantation in a drilled or punched bone hole. For example, a cylindrically-shaped implant with an internal cavity that is 4.0 mm in diameter and 25 mm long, with the drug stored in the cavity, would have an approximate volume of 0.31 ml available for the sex steroid and/or equivalent drug.

As discussed above under "Dosing", this would be a sufficient volume for the desired doses of exemplary drugs such as estradiol cypionate and testosterone undecanoate, and is within the appropriate range of other sex steroids and equivalents that may be used. The foregoing dimensions are exemplary only. Other implant embodiments may have other sizes, shapes, and/or volumes. Such implants are preferably capable, however, of holding about 0.10 ml to about 0.75 ml of drug composition, or more preferably about 0.15 ml to about 0.5 ml.

Textiles

Textiles suitable for use in delivering the one or more sex steroids and/or equivalents include sutures, tapes, meshes, sheets, fabrics, and the like. Such textiles may be formed by mechanical interdigitation of fibers (e.g., braiding, wrapping, knitting, weaving, spinning), melt-blowing, melt-spinning, electro-spinning, or felting fabrication techniques. A textile may be loaded with sex steroids and/or their equivalents by providing a solution or carrier including the sex steroids and/or their equivalents, and the solution being soaked into, coated onto, absorbed to, bonded to, or encapsulated by the textile in concentrations and volumes as described herein. Textiles may be placed at or near the surgical site in the vicinity of the enthesis so as to be able to locally deliver the drug composition loaded thereon.

The textiles used herein can be absorbable or non-absorbable. The textiles can be made of synthetic or natural fibers, or combination of both. The materials used for the fibers may include polyethylene, polyester, polypropylene, silk, nylon, collagen, polyglyconate, polydioxanone, polyglactin, polyglycolic acid, polylactic acid, polydioxanone, polydroxyalkanoate, poliglecaprone, polycaprolactone, or combinations thereof.

As one example of sizing and drug dosing, a suture tape is sized at 2 mm wide by 0.5 mm thick and 300 mm long. When the drug is coated on the surface at a thickness of about 0.3 mm, the tape includes 0.36 ml of available drug.

As discussed above under "Dosing", this would be a sufficient volume for the desired doses of exemplary drugs such as estradiol cypionate and testosterone undecanoate, and is within the appropriate range of other sex steroids and equivalents that may be used. The foregoing dimensions are exemplary only. Other textile embodiments may have other sizes, shapes, and/or drug volumes. Such textiles are preferably capable, however, of holding about 0.10 ml to about 0.75 ml of drug composition, or more preferably about 0.15 ml to about 0.5 ml of drug composition.

Patch

In another embodiment, a drug-eluting patch is placed in proximity to the enthesis, either adjacent to or attached to soft tissue. The patch may be used as a reinforcing augmentation patch as part of the repair construct itself via direct attachment to the proximate tendon or ligament portion of the enthesis.

The patch may comprise xenograft, allograft, autograft, synthetic materials, or combinations thereof. Xenograft materials may include ligamentous, tendinous, submucosal, pericardial, and/or dermal tissues. Allograft materials may include ligamentous, tendinous, fascial, and/or dermal tissues. Autograft materials may include ligamentous, tendinous, and/or fascial tissues. Suitable synthetic materials include the materials described above as suitable for a textile embodiment.

Similar to the textile embodiments, a patch may be loaded with a drug composition by providing a solution containing the desired set of sex steroids and/or equivalents, the solution being soaked into, coated onto, adsorbed to, bonded to, or encapsulated by the patch in concentrations and volumes as described herein.

In one exemplary embodiment, a patch is sized at 25 mm×25 mm×1 mm. At 50% porosity, such a patch has approximately 0.31 ml of storage space available for the drug composition. In another example, a patch sized at 25 mm×25 mm and with the drug coated on the surface at a thickness of 0.3 mm has approximately 0.375 ml of drug available.

As discussed above under "Dosing", this would be a sufficient volume for the desired doses of exemplary drugs such as estradiol cypionate and testosterone undecanoate, and is within the appropriate range of other sex steroids and equivalents that may be used. The foregoing dimensions are exemplary only. Other patch embodiments may have other sizes, shapes, and/or drug volumes. Such patches are preferably capable, however, of holding about 0.10 ml to about 0.75 ml of drug composition, or more preferably about 0.15 ml to about 0.5 ml of drug composition.

Drug Depot Formulations

In another embodiment of the present invention, sex steroids and/or equivalents are combined with a suitable carrier formulated to allow extended release of the drug throughout at least a portion of the healing period. Carriers may include, for example, salts, liposomes, polymeric micelles, microspheres, nanoparticles, or combinations thereof. Methods of attachment of the drug to the carrier include ionic bonding, covalent bonding, absorption, encapsulation, or integration into the bulk structure of the carrier, depending on the particular carrier(s) selected. The combination of the drug and the carrier as formulated to release the drug over a period of time may be referred to herein as a "depot drug".

In one embodiment, a depot drug is administered by local injection at a location proximate the enthesis. The drug dose may be set according to the "Dosing" section herein. The injection proximate to the enthesis can include: intra-articular, intra-osseous, intra-tendinous, and intra-bursal administration. For RCR, intra-articular injections are generally located anywhere in the glenohumeral joint, and preferably located in proximity to the superolateral humeral head. Intra-osseous injections are generally located in the proximal humerus, and preferably located in the greater tuberosity of the humerus. Intra-tendinous injections are located anywhere in the tendon, and for RCR procedures preferably located lateral to the musculotendinous junction. Intra-bursal injections are generally located in the subacromial space, and preferably located immediately superior to the rotator cuff tendon. Other anatomical structures may be targeted in situations where the target enthesis is not a rotator cuff tendon.

Additional Formulation Details

The drug formulations described herein may include solvents (aqueous or non-aqueous), solutions (aqueous or non-aqueous), emulsions (e.g., oil-in-water or water-in-oil), suspensions, dispersion and suspension media, coatings, and isotonic and absorption promoting or delaying agents. Aqueous and non-aqueous solvents, solutions, and suspensions may also include suspending agents and thickening agents.

Supplementary active compounds (e.g., preservatives, antibacterial, antiviral and antifungal agents) can also be incorporated into the formulations.

EXAMPLES

The following examples describe various studies that together support the conclusion that the administration of sex steroids and/or sex steroid equivalents to subjects with otherwise normal levels of sex steroids promotes healing of an enthesis. In particular, Example 5 unexpectedly demonstrated that the administration of sex steroids resulted in significant improvements in enthesis healing outcomes even though the test subjects were non-deficient in sex steroids. In other words, even though intuition suggests that there is no need to enhance sex steroids when the subject is already at normal levels, it was surprisingly found that providing a sex steroid to such a subject improved enthesis healing as compared to controls.

The scope of the invention is not limited by the particular examples presented, and those of skill in the art will readily recognize that other sex steroids and/or sex steroid equivalents would also be expected to provide similar beneficial results.

Figure 3:
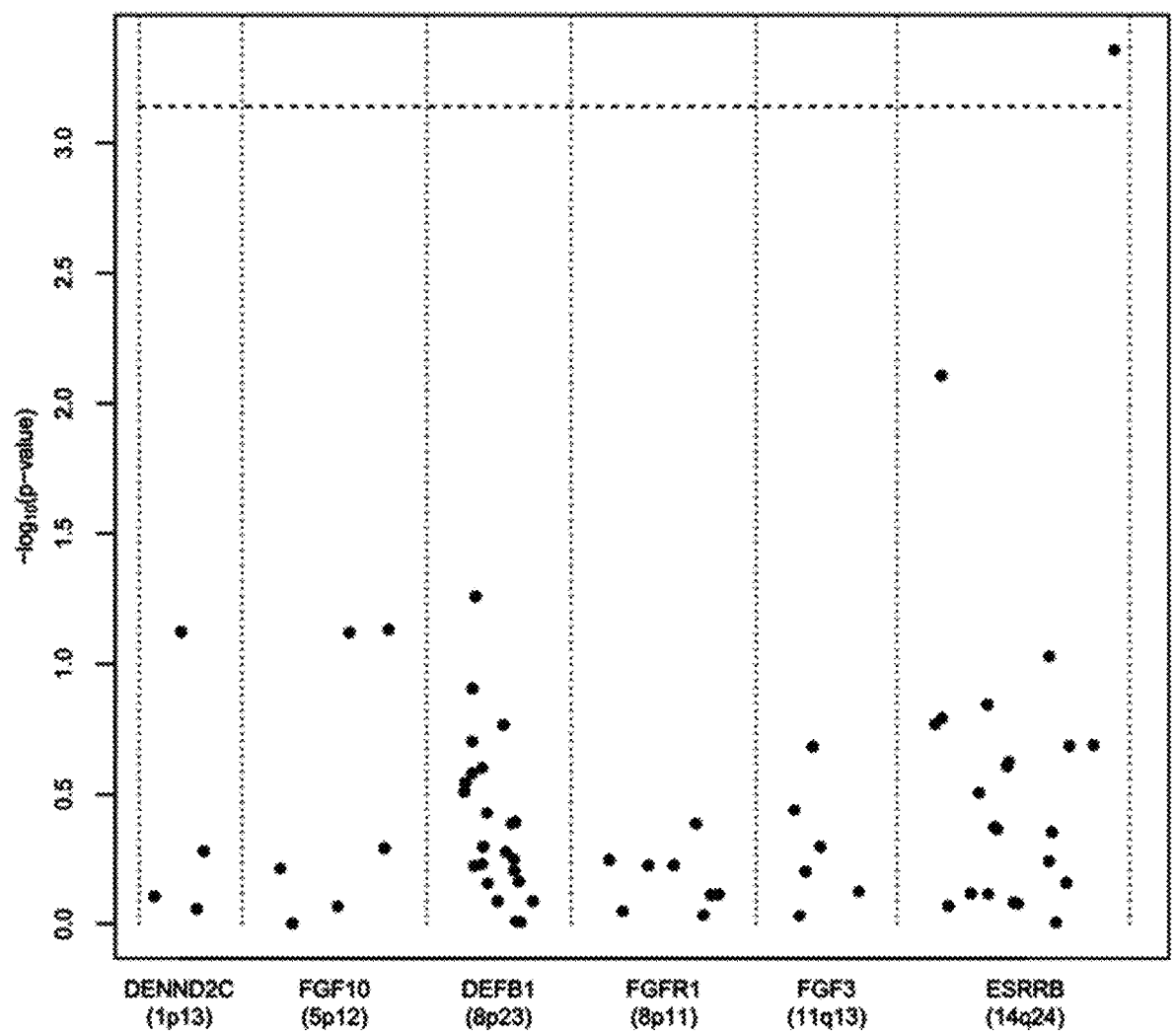
FIG. 3 is a −log 10 P values of SNP testing and rotator cuff disease, where horizontal dashed line denotes significance.

Example 1—Significant Association of a SNP Variant in the ESRRB Gene with Rotator Cuff Healing Failure Magnetic resonance imaging studies were performed at a minimum of 1 year postoperatively on 72 patients undergoing arthroscopic rotator cuff repair. Characteristics of cases with and without a family history of rotator cuff tearing were compared, and a comparison of the frequency of single nucleotide polymorphism ("SNP") 1758384 (in ESRRB) was performed between patients who healed and those who failed to heal. Using SNP genotyping testing, as shown in FIG. 3, it was demonstrated that rotator cuff tearing and failure of healing after rotator cuff repair is associated with a genetic polymorphism within estrogen-related receptor-β ("ESRRB"). (See Teerlink C C, Cannon-Albright L A, Tashjian R Z. Significant association of full-thickness rotator cuff tears and estrogen-related receptor-β (ESRRB). J Shoulder Elb Surg. 2015; Tashjian R Z, Granger E K, Zhang Y, Teerlink C C, Cannon-Albright L A. Identification of a genetic variant associated with rotator cuff repair healing. J Shoulder Elb Surg. 2016).

Example 2—Estrogen and Androgen Receptors are Expressed on Both Normal and Torn Rotator Cuff Tendons Supraspinatus tendon-edge biopsies were performed at the time of surgery on 24 patients undergoing supraspinatus repair and 9 patients undergoing open reduction and internal fixation for a proximal humerus fracture. Ribonucleic acid (RNA) was extracted and sequenced to determine gene expression within both the torn and untorn tendon at its attachment site to the bone, i.e. at the enthesis. Within the genes expressed in both torn and intact tendons are estrogen and androgen receptors. (Unpublished data, but experimental details described in Tashjian R Z, Lock I, Granger E K, Wang Y, Lee Y, Chalmers P N, Jones K B. Gene Expression in Torn Rotator Cuff Tendons Determined by RNA Sequencing. Orthop J Sports Med. 2020).

Figure 4A:
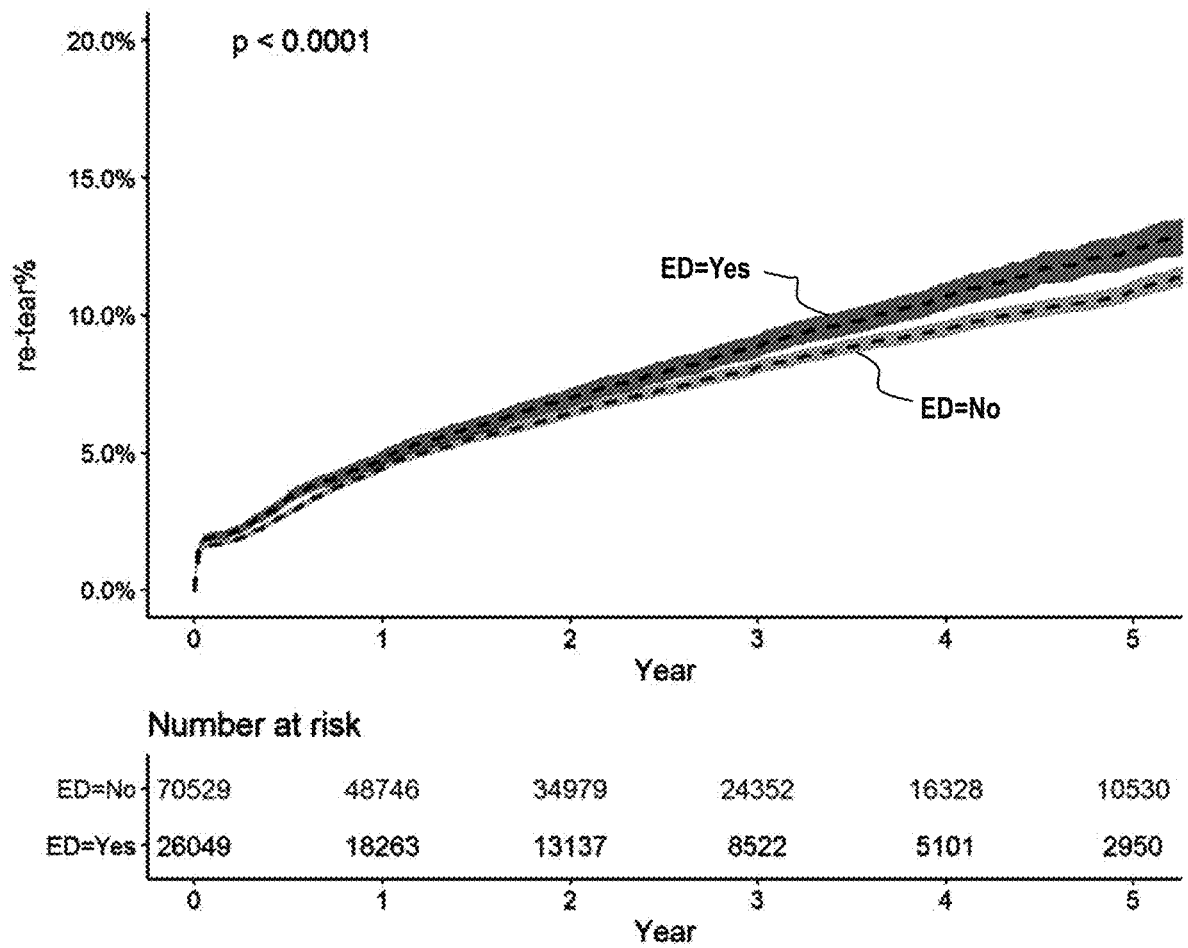
FIG. 4A is a Kaplan-Meier plot of cumulative incidence of surgery for healing failure after rotator cuff repair (re-tear %) in estrogen deficient (ED) vs. controls.

Example 3—People that are Estrogen or Testosterone Deficient have Higher Odds of Needing a Rotator Cuff Repair and Higher Odds of Having a Healing Failure after Rotator Cuff Repair A study within a multi-payor large national database with over 160 million individuals was conducted including 292,666 patients who underwent RCR and an equal number of controls matched for age, sex, year of surgery, and years within the database. Comparing groups, it was demonstrated that the odds of having an RCR in estrogen deficient patients was 48% higher (OR=1.48 [95% CI 1.44 to 1.51], p<0.001) than non-estrogen deficient patients after adjusting for age, sex, region, insurance plan type, occupation, tobacco use, number of years in the database, year, and Charleson-comorbidity index. This same study demonstrated that the risk of RCR healing failure requiring a subsequent surgery after RCR for estrogen deficient patients was 8% higher (HR=1.08 [95% CI 1.02 to 1.14], p=0.008) than non-estrogen deficient patients, as shown in FIG. 4A, after adjusting for the same variables.

The odds of having an RCR in testosterone deficient patients was 89% higher (OR=1.89 [95% CI 1.82 to 1.96], p<0.001) than non-testosterone deficient patients after adjusting for the same variables.

Figure 4B:
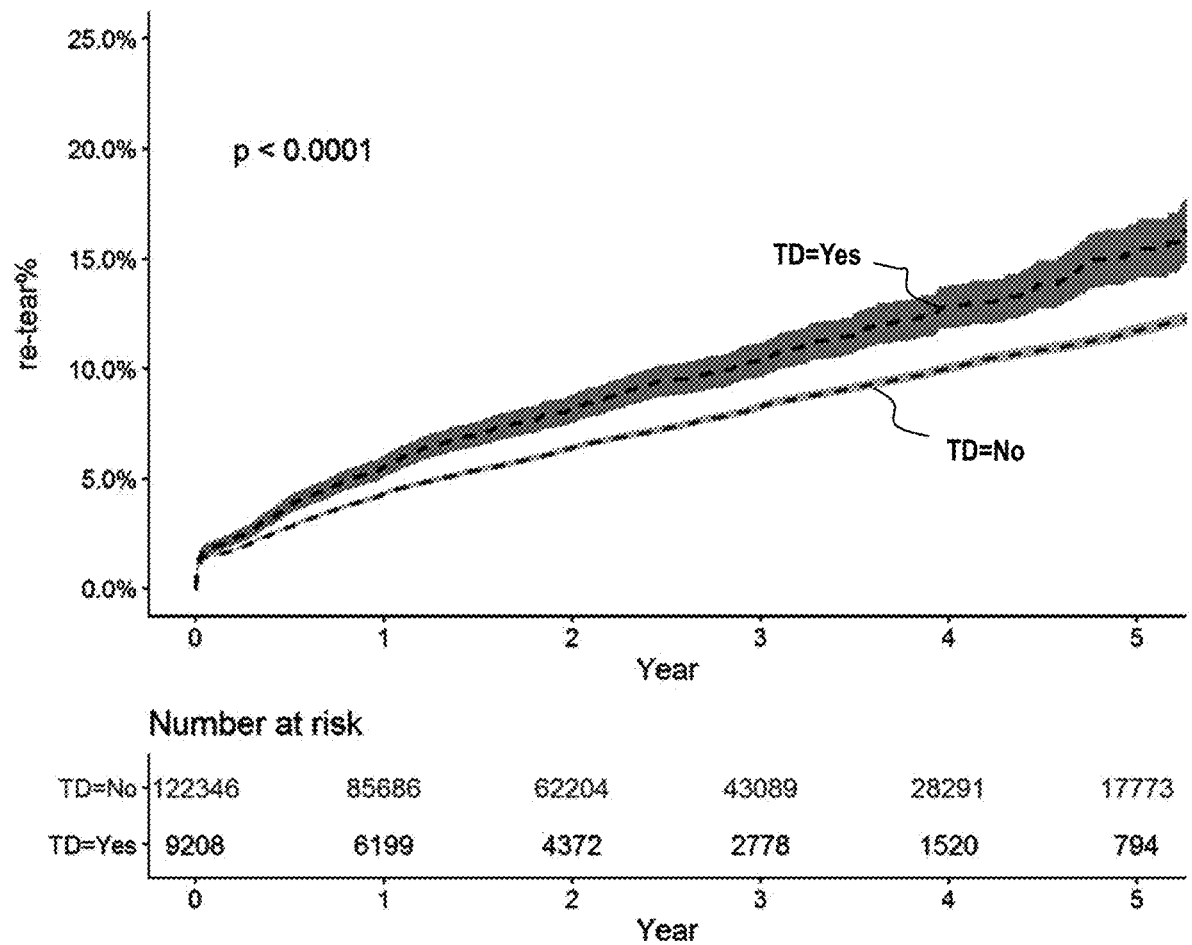
FIG. 4B is a Kaplan-Meier plot of cumulative incidence of surgery for healing failure after rotator cuff repair (re-tear %) in testosterone deficient (TD) vs. controls.

The risk of RCR healing failure requiring a subsequent surgery after RCR for testosterone deficient patients was 19% higher (HR=1.19 [95% CI 1.10 to 1.28], p<0.001), as shown in FIG. 4B, than non-testosterone deficient patients after adjusting for the same variables. Many surgeons will not perform RCR on patients who use tobacco out of concern that the failure risk is higher, but the association between RCR healing failure and testosterone deficiency was stronger than association between RCR healing failure and tobacco use (HR 1.14 [1.09 to 1.20], p<0.001). The combination of genetic, animal, and human empiric evidence is highly suggestive that sex hormone deficiency (SHD) plays a mechanistic role in RCR healing failure.

Figure 5:
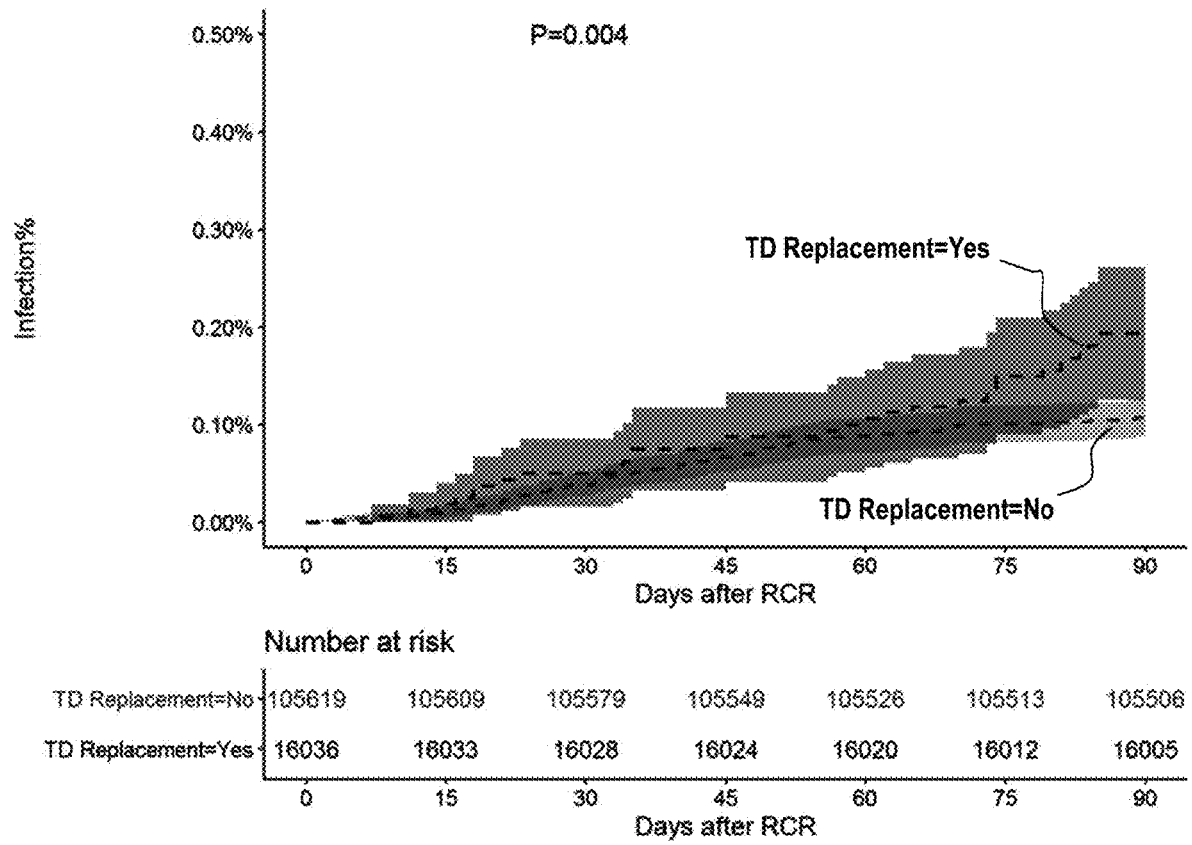
FIG. 5 is a Kaplan-Meier plots of cumulative incidence of infection after rotator cuff repair (Infection %) in testosterone deficient (TD) with replacement vs. controls.

Example 4—Patients Receiving Systemic Sex Hormone Replacement have a Higher Risk of Infection after Rotator Cuff Repair While the above examples suggest that testosterone deficiency is a strong contributor to rotator cuff tearing and RCR healing failure, systemic testosterone replacement may increase infection risk. The higher testosterone levels found in males as compared to females increase the presence of *Cutibacterium acnes* on the skin. (See Chalmers P N, Beck L, Stertz I, Tashjian R Z. Hydrogen peroxide skin preparation reduces *Cutibacterium acnes* in shoulder arthroplasty: a prospective, blinded, controlled trial. J Shoulder Elb Surg. Published online 2019; Rao A J, Chalmers P N, Cvetanovich G L, et al. Preoperative Doxycycline Does Not Reduce *Propionibacterium acnes* in Shoulder Arthroplasty. J Bone Jt Surg. 2018). Using the multi-payor large national database described in Example 3, it was demonstrated that the risk of having an infection after an RCR is increased by 75% in patients receiving testosterone replacement (HR 1.75 [1.17 to 2.62], 0.006), as shown in FIG. 5, as compared to non-testosterone replacement patients after adjusting for the same variables described above in Example 3.

Example 5—Estrogen Supplementation in Non-Estrogen Deficient Animals Improves Tendon Maturation Twenty-nine male wild type mice were randomly divided into three study groups. Group 1 (Control) consisted of unoperated mice which provided intact "control" shoulders with normal rotator cuff tendons. Group 2 (Repair Only) was a surgical repair group injected with the drug carrier used in Group 3. Group 3 (Repair+DES) was a surgical repair group injected with diethylstilbestrol (DES). Twenty-three mice were sacrificed four weeks post-operatively and used for histological analyses including scanning electron & light microscopy. The six remaining mice (n=3 Repair Only and n=3 Repair+DES) were sacrificed at 2 weeks for RNA expression analysis of various chondrogenic, angiogenic, osteogenic, tendon maturation/modulation, and hormonal genes.

The histological analyses demonstrated an increase of bone formation within the humeral head in the Repair+DES group compared to the Repair Only and the Control (intact tendon) groups (p<0.001). The areas of both the calcified and uncalcified fibrocartilage were significantly greater in the Repair Only group compared to the Control (intact tendon) and Repair+DES groups (p<0.03). When comparing the maximal thickness of calcified fibrocartilage to uncalcified fibrocartilage, the ratios for the Control (intact tendon), Repair Only, and Repair+DES groups were 2:1, 0.9:1 and 1.7:1, respectively. Collectively, the data suggests a less mature healing response in the Repair Only group compared to the Repair+DES group.

RNA expression data correlated with the histology demonstrating upregulation of chondrogenic, angiogenic and tendon modulation genes in the Repair Only group compared to Control (intact tendon) group (p<0.04 for all), and that addition of DES further increased the osteogenic, angiogenic, and tendon modulation gene expression compared to the Repair Only group (p<0.02).

Figures 6A, 6B, 6C:
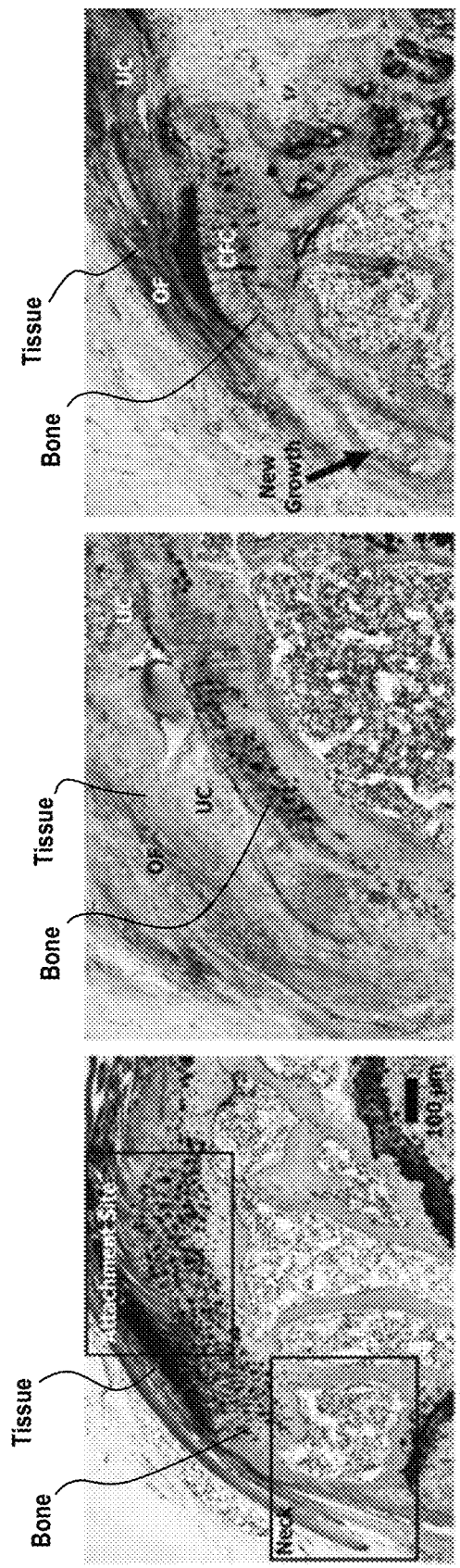
FIGS. 6A-6C are representative light microscopy micrographs of the control, repair only, and repair+DES subjects, respectively, illustrating the healing response at the tendon-bone interface and neck of the humerus, where OF=Organizing fibers, UC=unorganized chondral cites, and CFC=calcified fibrocartilage.

This study demonstrated that estrogen supplementation improved the maturation of the rotator cuff enthesis by maintaining a similar calcified to uncalcified fibrocartilage ratio as a native tendon enthesis. Estrogen supplementation further increased osteogenic, angiogenic and tendon maturation gene expression compared to standard repairs. Overall, these changes result in a tendon repair that resembles an intact tendon, as shown in FIGS. 6A-6C.

CONCLUSION

While certain embodiments of the present disclosure have been described in detail, with reference to specific configurations, parameters, components, elements, etcetera, the descriptions are illustrative and are not to be construed as limiting the scope of the claimed invention. Those of skill in the art can appreciate that the examples are intended to be exemplary only and that numerous changes, modifications, and alterations can be employed without departing from the scope of the presently disclosed subject matter.

All references cited herein, including, without limitation, patents, patent applications, and scientific references, are hereby incorporated by reference in their entirety.

Unless otherwise indicated, numbers expressing quantities, constituents, distances, or other measurements used in the specification and claims are to be understood as optionally being modified by the term "about" or its synonyms. When the terms "about," "approximately," "substantially," or the like are used in conjunction with a stated amount, value, or condition, it may be taken to mean an amount, value or condition that deviates by less than 20%, less than 10%, less than 5%, or less than 1% of the stated amount, value, or condition. At the very least, and not as an attempt to limit the application of the doctrine of equivalents to the scope of the claims, each numerical parameter should be construed in light of the number of reported significant digits and by applying ordinary rounding techniques.

Any headings and subheadings used herein are for organizational purposes only and are not meant to be used to limit the scope of the description or the claims.

It will also be noted that, as used in this specification and the appended claims, the singular forms "a," "an" and "the" do not exclude plural referents unless the context clearly dictates otherwise. Thus, for example, an embodiment referencing a singular referent (e.g., "widget") may also include two or more such referents.

It will also be appreciated that embodiments described herein may include properties, features (e.g., ingredients, components, members, elements, parts, and/or portions) described in other embodiments described herein. Accordingly, the various features of a given embodiment can be combined with and/or incorporated into other embodiments of the present disclosure. Thus, disclosure of certain features relative to a specific embodiment of the present disclosure should not be construed as limiting application or inclusion of said features to the specific embodiment. Rather, it will be appreciated that other embodiments can also include such features. Similarly, it should be understood that for any given element of component of a described embodiment, any of the possible alternatives listed for that element or component may generally be used individually or in combination with one another, unless implicitly or explicitly stated otherwise.

The invention claimed is:

1. A method of improving healing of an enthesis of a subject in need thereof, the method comprising:
   locally administering, at a site of enthesis repair, a composition comprising
   (i) an estrogen at a dose of 0.05 mg to 8 mg, wherein the estrogen comprises one or more of estrone, estradiol, estriol, or estradiol ester,
   (ii) an androgen and/or androgen equivalent at a dose of 2.5 mg to 200 mg, wherein the androgen comprises one or more of testosterone, dihydrotestosterone. androstenedione, or testosterone ester, and wherein the androgen equivalent is a selective androgen receptor modulator comprising one or more of enobosarm or ligandrol, or
   (iii) combination thereof,
   to thereby increase levels of at least one sex steroid at the site of enthesis repair; and
   the composition improving healing of the enthesis in the subject.

2. The method of claim 1, wherein the enthesis is a repaired enthesis.

3. The method of claim 2, wherein risk of re-tear injury is reduced due to the improved healing of the enthesis.

4. The method of claim 1, wherein the enthesis is associated with an Achilles tendon, rotator cuff tendon, distal biceps and triceps tendon, pectoralis major tendon, flexor and extensor tendon, wrist extensor and flexor tendon, hip abductor tendon, proximal hamstring tendon, patella tendon, quadriceps tendon, peroneal tendon, toe flexor and extensor tendon, anterior cruciate ligament, posterior cruciate ligament, knee medial and lateral collateral ligament, anterior talofibular ligament, calcaneofibular ligament, posterior talofibular ligament, anterior inferior tibiofibular ligament, posterior inferior tibiofibular ligament, ankle deltoid and spring ligament, acromioclavicular ligament, coracoclavicular ligament, sternoclavicular ligament, elbow lateral collateral ligament, elbow medial collateral ligament, radial annular ligament, ligament of the wrist, plantar plate, or collateral ligament of a finger, thumb, or toe.

5. The method of claim 1, wherein the composition causes upregulation of one or more chondrogenic, angiogenic, and/or tendon modulation genes.

6. The method of claim 1, wherein the composition further comprises an aromatase inhibitor.

7. The method of claim 1, wherein the composition comprises a combination of sex steroids and/or sex steroid equivalents formulated to increase levels of more than one sex steroid in the subject.

8. The method of claim 1, wherein the composition is administered by way of a drug-eluting implant implanted at or near the site of the enthesis.

9. The method of claim 8, wherein the drug-eluting implant is a suture, suture anchor, other implant configured for implantation in bone at or near the site of the enthesis, a drug-loaded textile, drug-loaded patch, or combination thereof.

10. The method of claim 1, wherein the composition further comprises a carrier and is formulated to provide extended release of the composition.

11. A method of improving healing of an enthesis of a subject in need thereof, the method comprising:

locally administering, at a site of enthesis repair, a composition consisting of:
(i) an estrogen, androgen equivalent, or combination thereof,
wherein the estrogen comprises one or more of estrone, estradiol, estriol, or estradiol ester,
wherein the androgen comprises one or more of testosterone, dihydrotestosterone. androstenedione, or testosterone ester,
wherein the androgen equivalent is a selective androgen receptor modulator comprising one or more of enobosarm or ligandrol, and
(ii) optionally, a carrier,
to thereby increase levels of at least one sex steroid at the site of enthesis repair; and
the composition improving healing of the enthesis in the subject.

12. The method of claim 11, wherein the carrier comprises a solvent, solution, emulsion, suspension, coating, isotonic agent, dispersion media, suspension media, absorption promoting agent, absorption delaying agent, suspending agent, thickening agent, preservative, antimicrobial agent, salt, liposome, polymeric micelle, microsphere, nanoparticles, or combination thereof.

13. The method of claim 11, wherein the composition is included in an implant, textile, patch, prodrug, or depot drug.

14. The method of claim 11, wherein administering the composition comprises administering:
(i) the estrogen at a dose of 0.05 mg to 8 mg,
(ii) the androgen and/or the androgen equivalent at a dose of 2.5 mg to 200 mg,
or combination thereof.

15. A method of improving healing of an enthesis of a subject, the method comprising:
locally administering, at a site of enthesis repair, a composition comprising an estrogen, androgen, androgen equivalent, or combination thereof to increase levels of at least one sex steroid at the site of enthesis repair,
wherein the composition omits other active compounds for improving healing of the enthesis,
wherein the estrogen comprises one or more of estrone, estradiol, estriol, or estradiol ester,
wherein the androgen comprises one or more of testosterone, dihydrotestosterone, androstenedione, or testosterone ester,
wherein the androgen equivalent is a selective androgen receptor modulator comprising one or more of enobosarm or ligandrol; and
the composition improving healing of the enthesis in the subject.

16. The method of claim 15, wherein administering the composition comprises administering:
(i) the estrogen at a dose of 0.05 mg to 8 mg,
(ii) the androgen and/or the androgen equivalent at a dose of 2.5 mg to 200 mg,
or combination thereof.

17. The method of claim 8, wherein locally administering the composition comprises placing the drug-eluting implant in a formed cavity in a bone.

18. The method of claim 1, wherein the estradiol ester comprises one or more of estradiol cypionate, estradiol benzoate, estradiol dipropionate, estradiol enanthate, estradiol undecylate, or estradiol valerate, and wherein the testosterone ester comprises testosterone enanthate, testosterone cypionate, testosterone propionate, or testosterone undecanoate.

19. The method of claim 11, wherein the estradiol ester comprises one or more of estradiol cypionate, estradiol benzoate, estradiol dipropionate, estradiol enanthate, estradiol undecylate, or estradiol valerate, and wherein the testosterone ester comprises testosterone enanthate, testosterone cypionate, testosterone propionate, or testosterone undecanoate.

20. The method of claim 15, wherein the estradiol ester comprises one or more of estradiol cypionate, estradiol benzoate, estradiol dipropionate, estradiol enanthate, estradiol undecylate, or estradiol valerate, and wherein the testosterone ester comprises testosterone enanthate, testosterone cypionate, testosterone propionate, or testosterone undecanoate.

* * * * *